United States Patent [19]

Weyer et al.

[11] Patent Number: 5,391,771
[45] Date of Patent: Feb. 21, 1995

[54] HYDROGENATION OF CITRIC ACID

[75] Inventors: Hans-Juergen Weyer, Mannheim; Rolf Fischer, Heidelberg; Christoph Sigwart, Schriesheim, all of Germany

[73] Assignee: BASF Aktiengesellschaft

[21] Appl. No.: 130,003

[22] Filed: Sep. 30, 1993

[30] Foreign Application Priority Data

Oct. 5, 1992 [DE] Germany ............................. 4233431

[51] Int. Cl.⁶ ..................... C07D 305/12; C07C 51/36; C07C 27/00
[52] U.S. Cl. ..................... 549/326; 549/427; 549/473; 549/497; 562/582; 562/584; 562/587; 562/592; 568/864
[58] Field of Search ............... 549/326, 323, 473, 497, 549/427; 562/582, 584, 597, 592; 568/864

[56] References Cited

U.S. PATENT DOCUMENTS 4,386,018  5/1983  Merger et al. ..................... 568/853
4,386,219  5/1983  Merger et al. ..................... 252/465
5,037,793  8/1991  Toussaint et al. ................... 502/308

FOREIGN PATENT DOCUMENTS 277562  1/1988  European Pat. Off. .
3854  11/1982  WIPO .

*Primary Examiner*—C. Warren Ivy
*Assistant Examiner*—Raymond Covington
*Attorney, Agent, or Firm*—John H. Shurtleff

[57] ABSTRACT

A process for the preparation of propane-1,2,3-tricarboxylic acid, tetrahydrofurfurylacetic acid and the $C_1$- to $C_{20}$-alkyl or $C_7$- to $C_{12}$-aralkyl esters thereof, propane-1,2,3-trimethanol, 3-methyltetrahydrofuran, 3-(2'-hydroxyethyl)tetrahydrofuran, 4-hydroxymethyltetrahydropyran, 2-methyl-γ-butyrolactone and/or 3-methyl-γ-butyrolactone, comprises reacting citric acid or the $C_1$- to $C_{20}$-alkyl or $C_7$- to $C_{12}$-aralkyl esters thereof on hydrogenation catalysts in non-aqueous solvents at from 50° to 400° C. and at from 1 to 400 bar.

14 Claims, No Drawings

HYDROGENATION OF CITRIC ACID

The present invention relates to a novel process for the preparation of propane-1,2,3-tricarboxylic acid, tetrahydrofurfurylacetic acid and the $C_1$- to $C_{20}$-alkyl or $C_7$- to $C_{12}$-aralkyl esters thereof, propane-1,2,3-trimethanol, 3-methyltetrahydrofuran, 3-(2'-hydroxyethyl)tetrahydrofuran, 4-hydroxymethyltetrahydropyran, 2-methyl-γ-butyrolactone and/or 3-methyl-γ-butyrolactone by the catalytic hydrogenation of citric acid and/or the $C_1$- to $C_{20}$-alkyl or $C_7$- to $C_{12}$-aralkyl esters thereof in non-aqueous solvents.

EP-A-277 562 discloses the catalytic hydrogenation of citric acid to give difunctional compounds such as 3-methyltetrahydrofuran and 3- and 4-methylbutyrolactone, but this specific process does not give any trifunctional compounds.

It is an object of the present invention to develop a process which overcomes the abovementioned disadvantages.

We have found that this object is achieved by a novel and improved process for the preparation of propane-1,2,3-tricarboxylic acid, tetrahydrofurfurylacetic acid and the $C_1$- to $C_{20}$-alkyl or $C_7$- to $C_{12}$-aralkyl esters thereof, propane-1,2,3-trimethanol, 3-methyltetrahydrofuran, 3-(2'-hydroxyethyl)tetrahydrofuran, 4-hydroxymethyltetrahydropyran, 2-methyl-γ-butyrolactone and/or 3-methyl-γ-butyrolactone, which comprises reacting citric acid or the $C_1$- to $C_{20}$-alkyl or $C_7$- to $C_{12}$-aralkyl esters thereof on hydrogenation catalysts in non-aqueous solvents at from 50° to 400° C. and at from 1 to 400 bar.

The process according to the invention can be carried out as follows:

Citric acid and/or the $C_1$- to $C_{20}$-alkyl or $C_7$- to $C_{12}$-aralkyl esters thereof can be reacted catalytically on hydrogenation catalysts in non-aqueous solvents at from 50° to 400° C., preferably from 150° to 300° C., and at from 1 to 400 bar, preferably from 50 to 300 bar.

Examples of suitable citric esters are monoesters, such as monomethyl citrate, monoethyl citrate, mono-n-propyl citrate, monoisopropyl citrate, mono-n-butyl citrate, monoisobutyl citrate, mono-sec-butyl citrate and mono-tert-butyl citrate, diesters, such as dimethyl citrate, diethyl citrate, di-n-propyl citrate, diisopropyl citrate, di-n-butyl citrate, diisobutyl citrate, di-sec-butyl citrate and di-tert-butyl citrate, and triesters, such as trimethyl citrate, triethyl citrate, tri-n-propyl citrate, triisopropyl citrate, tri-n-butyl citrate, triisobutyl citrate, tri-sec-butyl citrate, tri-tert-butyl citrate and tribenzyl citrate, and mixtures thereof. It is also possible to use all the compounds formed as intermediates in the novel hydrogenation. All these starting materials can be introduced into the process according to the invention in solid, liquid or gaseous form. Particular preference is given to the use of citric acid and trialkyl citrates, such as trialkyl citrates containing $C_1$- to $C_{20}$-alkyl groups, preferably trialkyl citrates containing $C_1$- to $C_8$-alkyl groups, for example trimethyl citrate, triethyl citrate, tri-n-propyl citrate, triisopropyl citrate, tri-n-butyl citrate, triisobutyl citrate, tri-sec-butyl citrate, tri-tert-butyl citrate, tri-n-hexyl citrate and triamyl citrate, particularly preferably trialkyl citrates containing $C_1$- to $C_4$-alkyl groups, for example trimethyl citrate, triethyl citrate, tri-n-propyl citrate, tri-isopropyl citrate, tri-n-butyl citrate, triisobutyl citrate, tri-sec-butyl citrate and tri-tert-butyl citrate.

The hydrogenation can be carried out in non-aqueous solvents, it also being possible for the citric acid and/or the esters thereof or the reaction products thereof to function as solvent; aqueous reaction systems are an exception.

Non-aqueous solvents are those to which water is not or has not been added. The non-aqueous solvents may be moist, i.e. they do not require drying, i.e. the removal of residual water (hygroscopicity). Examples of suitable non-aqueous solvents are ethers, such as dialkyl ethers, preferably dialkyl ethers containing $C_1$- to $C_{20}$-alkyl groups, particularly preferably dialkyl ethers containing $C_1$- to $C_8$-alkyl groups, e.g. diethyl ether, methyl tert-butyl ether, di-n-butyl ether, ethylene glycol dimethyl ether, ethylene glycol diethyl ether and diglyme, and cyclic ethers, such as 5- to 8-membered ring ethers, e.g. furan, tetrahydrofuran, pyran, dihydropyran and dioxane, preferably ethylene glycol dimethyl ether, ethylene glycol diethyl ether, tetrahydrofuran and dioxane, particularly preferably ethylene glycol diethyl ether and tetrahydrofuran, alcohols which are, for example, 70 to 100%, preferably $C_1$- to $C_6$-alkanols, such as methanol, ethanol, n-propanol, isopropanol, n-butanol, isobutanol, sec-butanol, tert-butanol, n-pentanol and n-hexanol, particularly preferably $C_1$- to $C_4$-alkanols, such as methanol, ethanol, n-propanol, isopropanol and n-butanol. It is also possible to employ any desired mixtures of the abovementioned solvents.

Suitable hydrogenation catalysts are all conventional catalysts, as described, for example, in Houben-Weyl, Methoden der organischen Chemie, Volume IV/1 c, Georg Thieme Verlag, Stuttgart, 1980. Perferred hydrogenation catalysts are those whose catalytically active material contains one or more metals from sub-group I, VII or VIII of the Periodic Table of the Elements, such as copper, silver, gold, manganese, rhenium, iron, cobalt, nickel, ruthenium, rhodium, palladium, osmium, iridium and platinum, preferably copper, iron, nickel, cobalt, palladium, platinum, rhodium and ruthenium, particularly preferably copper, palladium, ruthenium, nickel and cobalt, and, if desired, one or more metals from sub-groups II to VI of the Periodic Table of the Elements, such as zinc, cadmium, mercury, scandium, yttrium, lanthanum, titanium, zirconium, hafnium, vanadium, niobium, tantalum, chromium, molybdenum and tungsten, preferably zinc, chromium, molybdenum, lanthanum, zirconium and tungsten, particularly preferably zinc, chromium, molybdenum and tungsten, and, if desired, elements from main groups I and II of the Periodic Table of the Elements, such as lithium, sodium, potassium, rubidium, cesium, francium, magnesium, calcium, strontium, barium and radium, preferably lithium, sodium, potassium, magnesium and calcium.

These catalysts are generally in the form of their oxides in the hydrogenation and may additionally contain acids, such as phosphoric acid, sulfuric acid, hydrofluoric acid and heteropoly acids, preferably phosphoric acid and heteropoly acids, particularly preferably phosphoric acid.

The hydrogenation catalysts can be employed as homogeneous or preferably as heterogeneous catalysts. If heterogeneous catalysts are used, they can be employed either as supported catalysts or in compact form. The type of support material is generally not crucial; conventional support materials, such as silicon dioxide, aluminum oxides, titanium dioxide, zirconium dioxide, activated charcoal, silicates or zeolites, can be used. If necessary, binders or shaping auxiliaries can also be employed to prepare the catalysts.

In particular, noble-metal catalysts are usually employed on supports, such as charcoal (for example activated charcoal), aluminum oxide or zirconium dioxide, for example palladium on charcoal, palladium on aluminum oxide, platinum on charcoal, ruthenium on charcoal and ruthenium on zirconium dioxide.

The hydrogenation can be carried out in the gas or liquid phase, and either batchwise or, preferably, continuously. If a heterogeneous catalyst is used, it can be employed as a suspension or fixed-bed catalyst. Reactors which can be employed are stirred or tubular reactors. A tubular reactor with a fixed catalyst can be operated with upflow or downflow through the catalyst. Weight hourly space velocities of from 0.01 to 2 kg, in particular from 0.05 to 0.5 kg, of citric acid or derivatives thereof per liter of catalyst and per hour have proven successful.

Depending on the reaction conditions and the solvent and catalyst used, it is possible to preferentially prepare propane-1,2,3-tricarboxylic acid, tetrahydrofurfurylacetic acid and the $C_1$- to $C_{20}$-alkyl or $C_7$- to $C_{12}$-aralkyl esters thereof, propane-1,2,3-trimethanol, 3-methyltetrahydrofuran, 3-(2'-hydroxyethyl)tetrahydrofuran, 4-hydroxymethyltetrahydropyran, 2-methyl-γ-butyrolactone and/or 3-methyl-γ-butyrolactone:

In general, the formation of the trifunctional compounds propane-1,2,3-tricarboxylic acid, tetrahydrofurfurylacetic acid and the $C_1$- to $C_{20}$-alkyl or $C_7$- to $C_{12}$-aralkyl esters thereof, propane-1,2,3-trimethanol, 3-(2'-hydroxyethyl)tetrahydrofuran and 4-hydroxymethyltetrahydropyran is preferred if a reaction is carried out in alcoholic solvents and/or if citric esters are employed.

By contrast, the difunctional compounds 2-methyl-γ-butyrolactone, 3-methyl-γ-butyrolactone and 3-methyltetrahydrofuran are preferentially formed if citric acid is employed in ethereal solvents.

In general, low reaction temperatures and pressures and short residence times favor the formation of propane-1,2,3-tricarboxylic acid and esters thereof, since the tertiary hydroxyl group is cleaved off first. By contrast, high reaction temperatures and pressures and long residence times favor the formation of ethers 3-(2'-hydroxyethyl)tetrahydrofuran, 4-hydroxymethyltetrahydropyran and 3-methyltetrahydrofuran. Tetrahydrofurfurylacetic acid and the esters thereof are generally formed preferentially at moderate reaction temperatures, pressures and residence times. For the hydrogenation to propane-1,2,3-trimethanol, low reaction temperatures, high reaction pressures and short residence times are favorable. 2-Methyl-γ-butyrolactone and 3-methyl-γ-butyrolactone are preferentially formed at moderate reaction temperatures and pressures and short residence times.

Thus, propane-1,2,3-tricarboxylic acid and the esters thereof are generally preferentially formed at from 100° to 175° C., in particular at from 125° to 175° C., and at from 1 to 200 bar, in particular at from 10 to 100 bar.

Tetrahydrofurfurylacetic acid and the esters thereof are preferentially formed at from 125° to 250° C., in particular at from 150° to 200° C., and at from 1 to 200 bar, in particular at from 50 to 150 bar.

Propane-1,2,3-trimethanol is preferentially formed at from 100° to 250° C., in particular at from 125° to 175° C., and at from 100 to 400 bar, in particular at from 150 to 300 bar.

2-Methyl-γ-butyrolactone and 3-methyl-γ-butyrolactone are preferentially formed at from 100° to 200° C., in particular at from 125° to 175° C., and at from 50 to 400 bar, in particular at from 100 to 300 bar.

3-(2'-Hydroxyethyl)tetrahydrofuran, 4-hydroxymethyltetrahydropyran and 3-methyltetrahydrofuran are preferentially formed at from 150° to 300° C., in particular at from 175° to 275° C., and at from 100 to 400 bar, in particular at from 200 to 300 bar.

The respective reaction conditions under which the individual products are preferentially formed are highly dependent on the catalysts used.

The removal of the tertiary hydroxyl group and the formation of tetrahydrofuran and tetrahydropyran are promoted by the presence of acidic substances.

The products which can be prepared by the process according to the invention belong to the group consisting of the tricarboxylic acids, triols and etherols and are used, for example, in the preparation of polyethers (Römpps Chemie-Lexikon, 8th Edition, p. 3287, Stuttgart, 1987; Houben-Weyl, Vol. 14/2, Stuttgart, 1963, p. 580; Ullmann's Encyklopädie der technischen Chemie, 3rd Edition, Munich, 1963, p. 43), Polyesters (Ullmann's Encyklopädie der technischen Chemie, Munich, 1963, Vol. 14, p. 80; Römpps Chemie-Lexikon, Stuttgart, 1987, p. 3285; Houben-Weyl, Vol. 14/2, Stuttgart, 1963, p. 1) and polyurethanes (Römpp, p. 3318; Houben-Weyl, Vol. 14/2, p. 57; Ullmann, Vol. 14, p. 338) as comonomers.

EXAMPLES

The catalysts employed in the examples have the following composition in the non-reduced state:

TABLE 1

| Catalyst | Shape | Composition |
|---|---|---|
| A<br>EP-A-100 406 | 4-mm pellets | 67% by weight of CoO, 19% by weight of Cuo, 7% by weight of $Mn_2O_3$, 3% by weight of $MoO_3$, 0.2% by weight of $Na_2O$, 3% by weight of $H_3PO_4$ |
| B<br>EP-A-44 444 | 4-mm pellets | 56% by weight of CuO, 44% by weight of $Al_2O_3$ |
| C<br>US-A-5 037 793 | 3-mm tablets | 50% by weight of NiO, 17% by weight of CuO, 31% by weight of $Al_2O_3$, 2% by weight of $MoO_3$ |
| D<br>DE-A-869 052 | 3-mm tablets | 37% by weight of CuO, 1% by weight of Bao, 1% by weight of $Cr_2O_3$, 0.4% by weight of ZnO, 15% by weight of MgO, 29% by weight of $SiO_2$ |
| E | powder | 5% by weight of Pd, 95% by weight C |
| F<br>DE-A-14 42 981 | 4-mm tablets | 40% by weight of CuO, 20% by weight of ZnO, 40% by weight of $Al_2O_3$ |
| G<br>EP-A-44 444 | 4-mm pellets | 82.4% by weight of CuO, 17.6% by weight of $Al_2O_3$ |
| H<br>DE-A-15 42 632 | 3-mm tablets | 70% by weight of CuO, 25% by weight of ZnO, 5% by weight of $Al_2O_3$ |
| K | 4-mm pellets | 0.5% by weight of Pd, 99.5% by weight of $Al_2O_3$ |
| L<br>EP-A-382-049 | 4-mm pellets | 10% by weight of NiO, 10% by weight of CoO, 4% by weight of CuO, 76% by weight of $ZrO_2$ |
| M<br>US-A-5 037 793 | 4-mm pellets | 50% by weight of NiO, 17% by weight of CuO, 31% by weight of $ZrO_2$, 2% by weight of $MoO_3$ |
| N<br>US-A-5 037 793 | 4-mm pellets | 50% by weight of NiO, 17% by weight of CuO, 31% by weight of $Al_2O_3$, 2% by weight of $MoO_3$ |
| P<br>EP-A-9768 | 4-mm pellets | 77.7% by weight of NiO, 22.3% by weight of $Al_2O_3$ |

Catalysts A to D, F to H and L to P were reduced in a stream of hydrogen before use.

The yields below were determined by gas chromatography.

EXAMPLE 1

400 ml of triethyl citrate were hydrogenated at 225° C. and 200 bar together with 1100 ml of tetrahydrofuran and 60 g of catalyst C (3-mm tablets) until the take-up of hydrogen had ceased. The reaction product was freed from tetrahydrofuran and ethanol and distilled under reduced pressure. The main product obtained was 118 g (61%) of 3-(2'-hydroxyethyl)tetrahydrofuran. In addition, 4 g (2%) of 4-hydroxymethyltetrahydropyran were formed.

EXAMPLE 2

400 g of citric acid were dissolved in 1000 ml of n-butanol and hydrogenated at 250° C. and 200 bar together with 60 g of catalyst A (4-mm pellets) until the take-up of hydrogen had ceased. The reaction product was freed from n-butanol and ethanol and distilled under reduced pressure, giving 99 g (52%) of 3-(2'-hydroxyethyl)tetrahydrofuran and 2.9 g (1.5%) of 4-hydroxymethyltetrahydropyran.

EXAMPLE 3

400 ml of triethyl citrate were hydrogenated at 175° C. and 10 bar together with 1100 ml of ethanol and 60 g of catalyst B (4-mm pellets) until the take-up of hydrogen had ceased. The reaction product was freed from ethanol and distilled under reduced pressure, giving 231.8 g (54%) of triethyl 1,2,3-propanetricarboxylate.

EXAMPLE 4

400 ml of triethyl citrate were hydrogenated at 200° C. and 200 bar together with 1100 ml of ethanol and 60 g of catalyst B (4-mm pellets) until the take-up of hydrogen had ceased. The reaction product was freed from ethanol and distilled under reduced pressure, giving 80 g (42%) of 3-(2'-hydroxyethyl)tetrahydrofuran and 1.8 g (1%) of 4-hydroxymethyltetrahydropyran.

EXAMPLE 5

400 ml of triethyl citrate were hydrogenated at 225° C. and 200 bar together with 1100 ml of tetrahydrofuran and 60 g of catalyst H (3-mm tablets) until the take-up of hydrogen had ceased. The reaction product was freed from tetrahydrofuran and ethanol and distilled under reduced pressure, giving 93.6 g (49%) of 3-(2'-hydroxyethyl)tetrahydrofuran and 6.8 g (3.6%) of 4-hydroxymethyltetrahydropyran.

EXAMPLE 6

400 ml of triethyl citrate were hydrogenated at 200° C. and 50 bar together with 1100 ml of ethanol and 10 g of catalyst E (powder) until the take-up of hydrogen had ceased. The reaction product was freed from ethanol and distilled under reduced pressure, giving 166.1 g (38%) of triethyl propanetricarboxylate.

EXAMPLE 7

400 ml of triethyl citrate were hydrogenated at 150° C. at 200 bar together with 1100 ml of tetrahydrofuran and 60 g of catalyst D (3-mm tablets) until the take-up of hydrogen had ceased. The reaction product was freed from tetrahydrofuran and distilled under reduced pressure, giving 87 g (39%) of propane-1,2,3-trimethanol and 41.6 g (19%) of 3-(2'-hydroxyethyl)tetrahydrofuran.

EXAMPLE 8

400 ml of triethyl citrate were hydrogenated at 175° C. and 50 bar together with 1100 ml of tetrahydrofuran and 60 g of catalyst F (4-mm tablets) until the take-up of hydrogen had ceased. The reaction product was freed from tetrahydrofuran and distilled under reduced pressure, giving 101 g (39%) of ethyl tetrahydrofurfurylacetate and 57 g (30%) of 3-(2'-hydroxyethyl)tetrahydrofuran.

EXAMPLE 9

400 ml of triethyl citrate were hydrogenated at 175° C. and 10 bar together with 1100 ml of tetrahydrofuran and 60 g of catalyst G (4-mm tablets) until the take-up of hydrogen had ceased. The reaction product was freed from ethanol and distilled under reduced pressure, giving 193 g (45%) of triethyl propane-1,2,3-tricarboxylate.

EXAMPLES 10 TO 16

70 g of citric acid were hydrogenated at 200 bar and at the hydrogenation temperature shown in Table 2 together with 1000 ml of ethylene glycol dimethyl ether and 50 ml of catalyst until the take-up of hydrogen had ceased.

TABLE 2

| Example No. | Catalyst | Temperature [°C.] | Yield [%] | | |
|---|---|---|---|---|---|
| | | | 3-MTHF | 2-MBL | 3-MBL |
| 10 | K | 175 | 0 | 32 | 45 |
| 11 | E | 175 | 0 | 31 | 44 |
| 12 | M | 225 | 86 | 0 | 0 |
| 13 | N | 225 | 60 | 0 | 0 |
| 14 | B | 225 | 54 | 0 | 0 |
| 15 | N | 225 | 61 | 0 | 0 |
| 16 | P | 175 | 0 | 43 | 40 |

3-MTHF = 3-methyltetrahydrofuran
2-MBL = 2-methylbutyrolactone
3-MBL = 3-methylbutyrolactone

We claim:

1. A process for the preparation of propane-1,2,3-tricarboxylic acid, tetrahydrofurfurylacetic acid and its $C_1$- to $C_{20}$-alkyl or $C_7$- to $C_{12}$-aralkyl ester derivatives, propane-1,2,3-trimethanol, 3-methyltetrahydrofuran, 3-(2'-hydroxyethyl)tetrahydrofuran, 4-hydroxymethyltetrahydropyran, 2-methyl-γ-butyrolactone and/or 3-methyl-γ-butyrolactone, which comprises:

reacting citric acid or the $C_1$- to $C_{20}$-alkyl or $C_7$- to $C_{12}$-aralkyl esters thereof on a hydrogenation catalyst in a nonaqueous reaction system which consists essentially of an organic solvent and excludes water as a solvent, at a temperature of from 50° to 400° C. and under a pressure of from 1 to 400 bar.

2. A process as claimed in claim 1, wherein hydrogenation catalysts are employed whose catalytically active material contains one or more elements from sub-group I, VII or VIII of the Periodic Table of the Elements.

3. A process as claimed in claim 1, wherein hydrogenation catalysts are employed whose catalytically active material contains one or more elements from sub-group I, VII or VIII of the Periodic Table of the Elements and one or more elements from sub-groups II to VI of the Periodic Table of the Elements.

4. A process as claimed in claim 1, wherein hydrogenation catalysts are employed which contain copper, cobalt, palladium, nickel and/or ruthenium.

5. A process as claimed in claim 1, wherein hydrogenation catalysts are employed which contain copper and/or one or more elements from sub-group VIII and molybdenum, tungsten, manganese and/or zinc.

6. A process as claimed in claim 1, wherein the catalytic hydrogenation is carried out at from 150° to 300° C. and at from 50 to 300 bar.

7. A process as claimed in claim 1, wherein the derivatives of citric acid are monoesters, diesters and/or triesters.

8. A process as claimed in claim 1, wherein the organic solvent is selected from the group consisting of alcohols, ethers and mixtures thereof.

9. A process as claimed in claim 1, wherein the organic solvent is ethylene glycol dimethyl ether, ethylene glycol diethyl ether, tetrahydrofuran or dioxane.

10. A process as claimed in claim 1, wherein the organic solvent is a $C_1$- to $C_4$-alkanol.

11. A process as claimed in claim 1, wherein the organic solvent is ethylene glycol dimethyl ether.

12. A process as claimed in claim 1, wherein the organic solvent is tetrahydrofuran.

13. A process as claimed in claim 1, wherein citric acid is used as the reactant.

14. A process as claimed in claim 1, wherein an alkyl or aralkyl ester of citric acid is used as the reactant.

* * * * *